(12) United States Patent
Hanson (10) Patent No.: US 11,911,248 B2
(45) Date of Patent: Feb. 27, 2024

(54) BREAST PAD (71) Applicant: Hallan Hanson, Brooklyn, NY (US)

(72) Inventor: Hallan Hanson, Brooklyn, NY (US)

(73) Assignee: Hallan Hanson, Brooklyn, NY (US)

( * ) Notice: Subject to any disclaimer, the term of this patent is extended or adjusted under 35 U.S.C. 154(b) by 905 days.

(21) Appl. No.: 16/875,831

(22) Filed: May 15, 2020

(65) Prior Publication Data

US 2020/0360197 A1  Nov. 19, 2020

Related U.S. Application Data

(60) Provisional application No. 62/848,913, filed on May 16, 2019.

(51) Int. Cl.
| | |
|---|---|
| A61F 13/14 | (2006.01) |
| A61F 13/539 | (2006.01) |
| A61F 13/513 | (2006.01) |
| A61F 13/514 | (2006.01) |
| A61F 13/84 | (2006.01) |
| A61F 13/15 | (2006.01) |
| A61F 13/53 | (2006.01) |
| A61F 13/511 | (2006.01) |

(52) U.S. Cl.
CPC ...... *A61F 13/513* (2013.01); *A61F 13/51456* (2013.01); *A61F 13/539* (2013.01); *A61F 13/8405* (2013.01); *A61F 2013/15016* (2013.01); *A61F 2013/1591* (2013.01); *A61F 2013/15878* (2013.01); *A61F 2013/51147* (2013.01); *A61F 2013/51366* (2013.01); *A61F 2013/530036* (2013.01); *A61F 2013/530802* (2013.01); *A61F 2013/8414* (2013.01)

(58) Field of Classification Search
CPC .. A61F 13/51; A61F 13/53717; A61F 13/539; A61F 13/8405; A61F 2013/15016; A61F 2013/51042; A61F 2013/51047; A61F 2013/51366; A61F 2013/53908; A61F 2013/5395; A61F 2013/53958; A61F 2013/53991; A61F 2013/8414
See application file for complete search history.

(56) References Cited

U.S. PATENT DOCUMENTS

| | | | |
|---|---|---|---|
| 4,125,114 A | * | 11/1978 | Repke ............... A61F 13/141 604/385.07 |
| 4,892,532 A | | 1/1990 | Boman |
| 5,149,336 A | | 9/1992 | Clarke et al. |

(Continued)

*Primary Examiner* — Catharine L Anderson
(74) *Attorney, Agent, or Firm* — Stinson LLP (57) ABSTRACT

A breast pad for receiving fluid leaked from a subject's breast includes an inner layer disposed for contacting the subject's breast. The inner layer has an inner surface and an outer surface opposite the inner surface. The inner layer includes wicking material for wicking fluid from the inner surface to the outer surface away from the subject's breast. An intermediate layer is disposed over the outer surface of the inner layer. The intermediate layer includes an absorbent material for absorbing the fluid wicked from the subject's breast by the wicking material of the inner layer. An outer layer is disposed over the intermediate layer. The outer layer includes a liquid-impermeable material for trapping the fluid absorbed by the intermediate layer within the breast pad.

18 Claims, 6 Drawing Sheets

(56) References Cited

U.S. PATENT DOCUMENTS

| | | | |
|---|---|---|---|
| 5,843,062 A * | 12/1998 | Reidmiller | A61F 13/141 |
| | | | 604/385.07 |
| 6,074,272 A | 6/2000 | Herbert | |
| H2062 H * | 4/2003 | Blaney | 602/46 |
| 7,311,583 B2 * | 12/2007 | Jagaric | A41C 3/144 |
| | | | 450/39 |
| 7,442,110 B2 | 10/2008 | Gaudet et al. | |
| 7,988,526 B2 | 8/2011 | Gransberry | |
| 8,419,502 B2 | 4/2013 | Lin | |
| 8,487,026 B2 * | 7/2013 | Bach | A61L 15/58 |
| | | | 526/348.3 |
| 2003/0212359 A1 * | 11/2003 | Butler | A61F 13/146 |
| | | | 602/48 |
| 2003/0220048 A1 * | 11/2003 | Toro | A61F 13/141 |
| | | | 450/57 |
| 2006/0154567 A1 * | 7/2006 | Jung-Shun | A41C 5/005 |
| | | | 450/39 |
| 2008/0200096 A1 * | 8/2008 | Thornton | A61F 13/141 |
| | | | 450/37 |
| 2015/0117877 A1 | 1/2015 | Cholet et al. | |
| 2015/0335497 A1 * | 11/2015 | Montford | A61F 13/505 |
| | | | 604/385.14 |

* cited by examiner

BREAST PAD

CROSS-REFERENCE TO RELATED APPLICATION

This application claims priority to U.S. Provisional Patent Application Ser. No. 62/848,913, filed May 16, 2019, which is hereby incorporated by reference in its entirety.

FIELD

The present invention generally relates to a breast/nursing pad, and more particularly, to a reusable, multilayered breast/nursing pad construed by thermoforming for absorbing breast milk from a subject's breast.

BACKGROUND

Devices for preventing breast milk from leaking onto exterior garments are well known. Breast/nursing pads are a commonly used device for placement over a subject's nipple, and often inside of a brassier or similar undergarment, to receive and absorb secreted breast milk so that the milk does not contact the other garments worn by the subject. Breast/nursing pads typically fall into the category of reusable pads and disposable pads.

SUMMARY

In one aspect, a breast pad for receiving fluid leaked from a subject's breast generally comprises an inner layer disposed for contacting the subject's breast. The inner layer has an inner surface and an outer surface opposite the inner surface. The inner layer comprises wicking material for wicking fluid from the inner surface to the outer surface away from the subject's breast. An intermediate layer is disposed over the outer surface of the inner layer. The intermediate layer comprises an absorbent material for absorbing the fluid wicked from the subject's breast by the wicking material of the inner layer. An outer layer is disposed over the intermediate layer. The outer layer comprises a liquid-impermeable material for trapping the fluid absorbed by the intermediate layer within the breast pad.

In another aspect, a breast pad for receiving fluid leaked from a subject's breast generally comprises a wicking layer. An absorbent layer is disposed over the wicking layer. A liquid-impermeable layer is disposed over the absorbent layer. The layers are thermoformed to bond the layers together.

In yet another aspect, a method of making a breast pad generally comprises providing a wicking layer and overlaying an absorbent layer on the wicking layer. A liquid-impermeable outer layer is overlaid on the absorbent layer. The wicking layer, absorbent layer, and outer layer are pressed together in a mold. The wicking layer, absorbent layer, and outer layer are heated in the mold to deform and set the layers into a desired shape.

BRIEF DESCRIPTION OF THE DRAWINGS

Corresponding reference characters indicate corresponding parts throughout the drawings.

DESCRIPTION OF THE PREFERRED EMBODIMENTS

Figure 1:
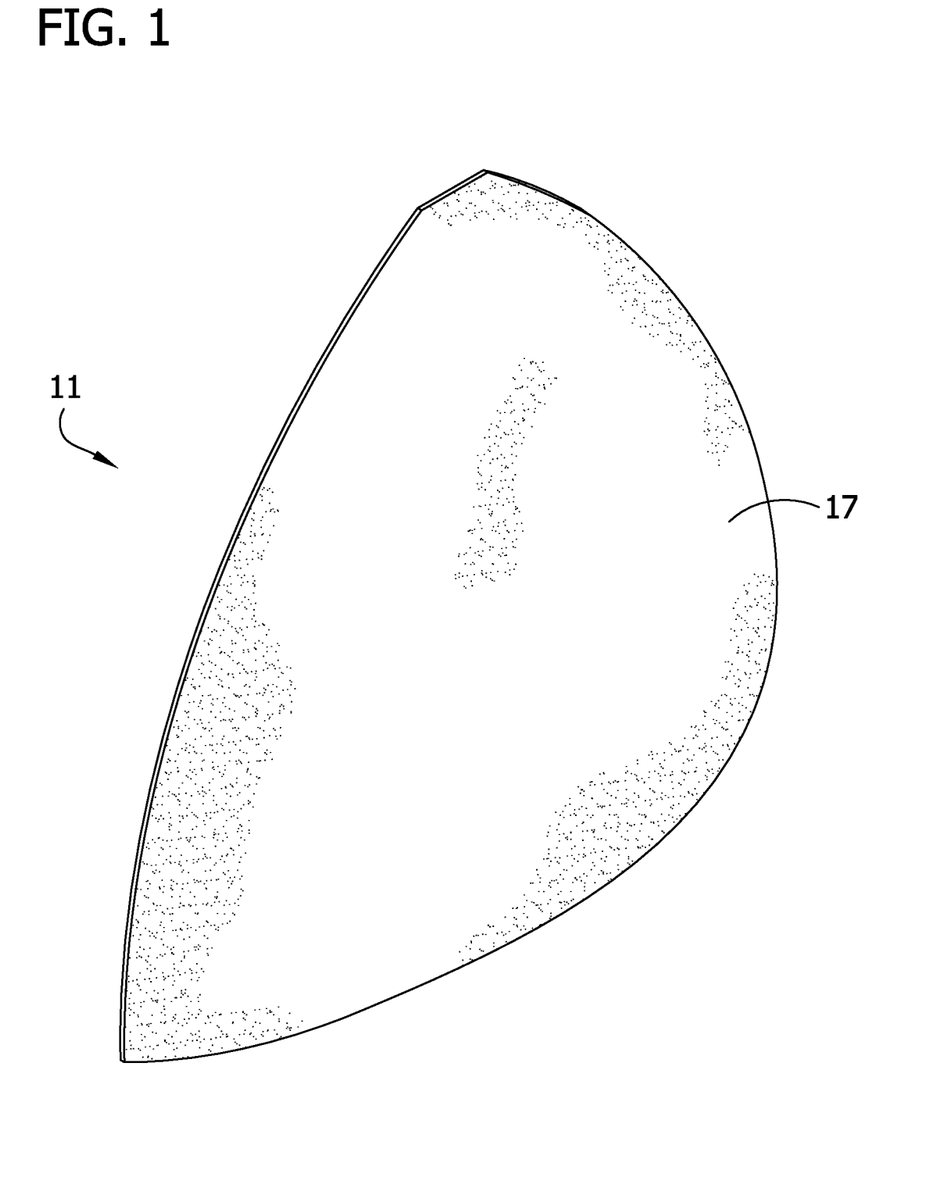
FIG. 1 is a perspective of a breast pad.
Figure 2:
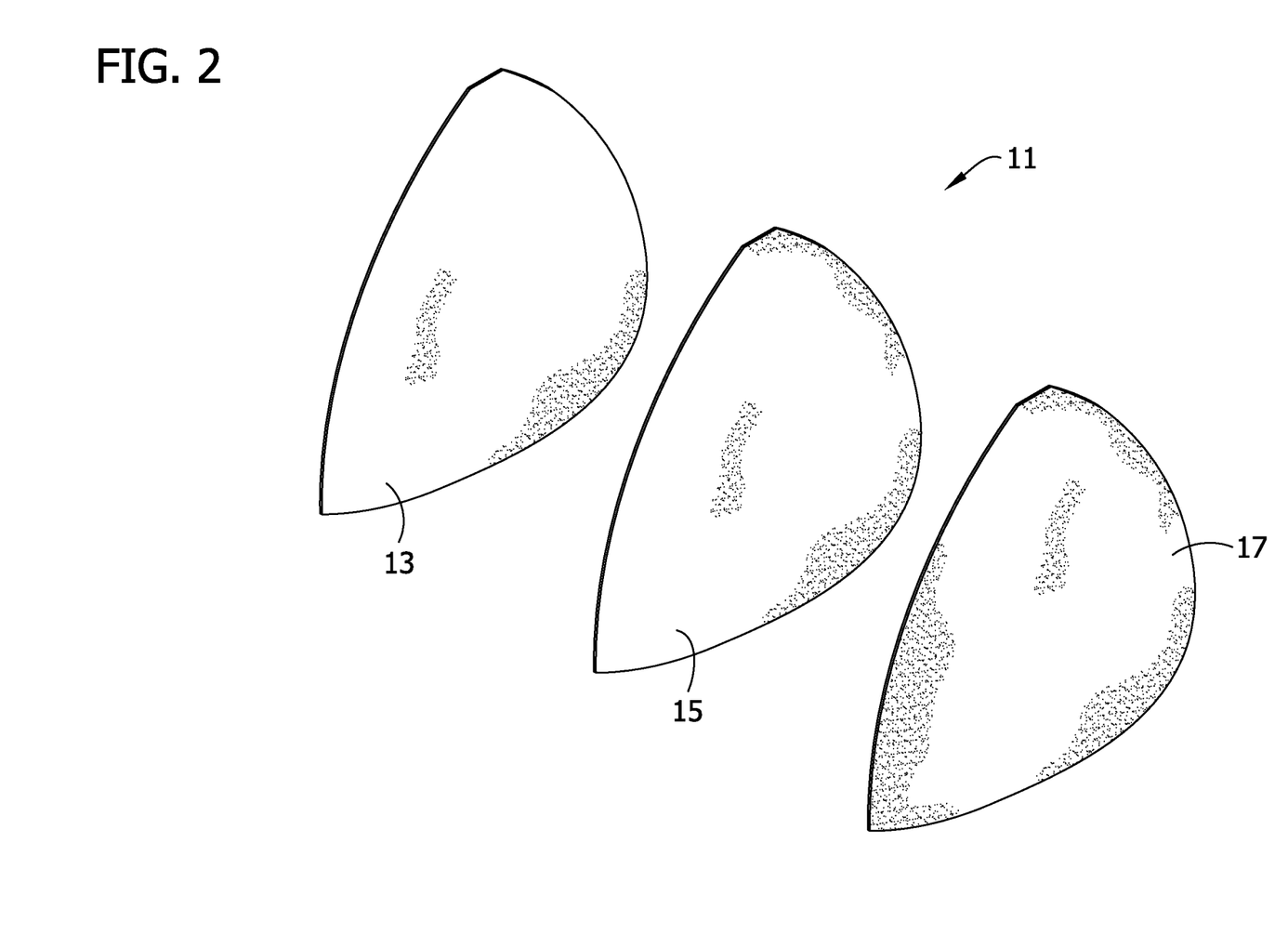
FIG. 2 is an exploded view of the breast pad.

Referring to FIGS. 1 and 2, a breast/nursing pad of the present disclosure is generally indicated at 11. The pad is configured to be applied over a subject's breast to absorb lacteal fluid (i.e., breast milk) secreted from the subject's breast. In the illustrated embodiment, the pad 11 is a separate pad structure configured for placement within an undergarment such as a brassier or the like. However, it will be understood that the pad 11 could be formed as part of a brassier or similar garment without departing from the scope of the disclosure.

In the illustrated embodiment, the pad 11 comprises three layers of material secured together. In particular, the pad 11 comprises an inner layer, generally indicated at 13, on which an intermediate layer, generally indicated at 15, is overlaid. An outer layer or cover generally indicated at 17, overlies and is secured to the intermediate layer 15. As will be explained in greater detail below, the layers 13-17 may be secured together in any suitable manner such as by radiofrequency welding, or other chemical and/or mechanical process. In a preferred embodiment, the layers 13-17 are bonded together through a thermoforming process.

In use, the inner layer 13 is disposed most adjacent or proximal to the subject's breast and is in contact with the breast, and the outer cover 17 is most distant or distal from the breast. However, the scope of the present invention is not limited to three layers. In addition, it is understood that the configuration of the layers of the pad can be different from that disclosed in the illustrated embodiment. Thus, while a specific configuration of layers is described, it should be appreciated that other configurations of the pad 11 are also within the scope of this disclosure.

Figure 3:
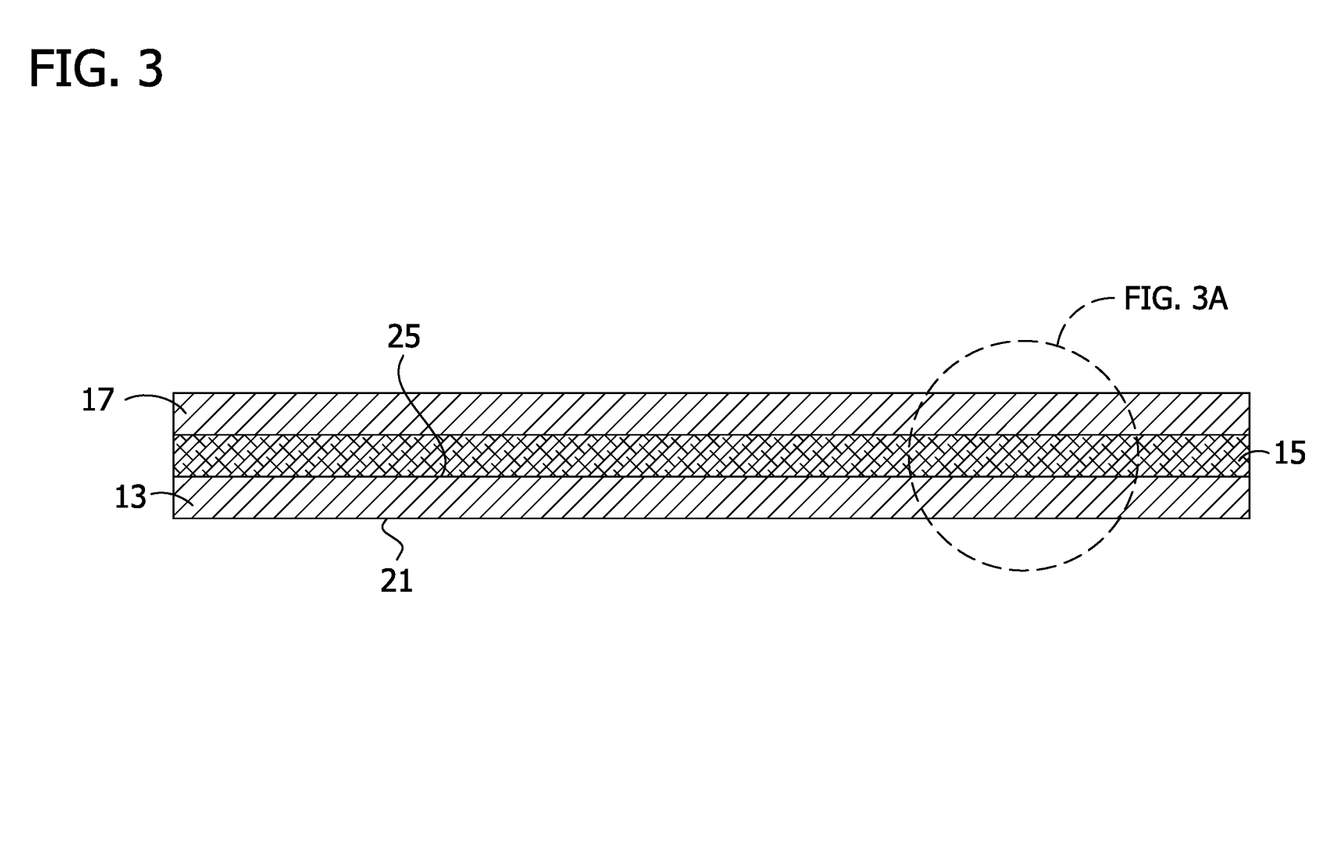
FIG. 3 is a schematic illustration of a section of a portion of the breast pad.
Figure 3A:
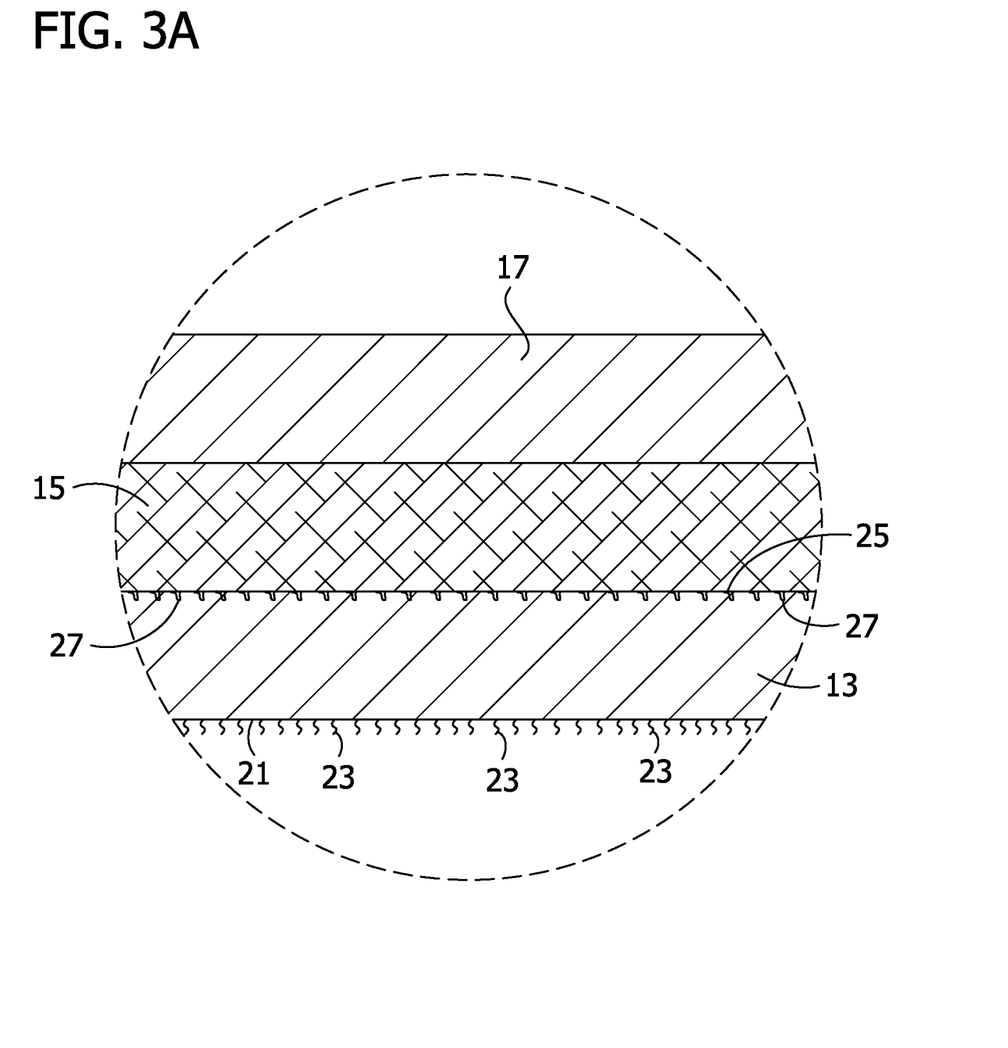
FIG. 3A is an enlarged fragmentary view of FIG. 3.
Figure 3B:
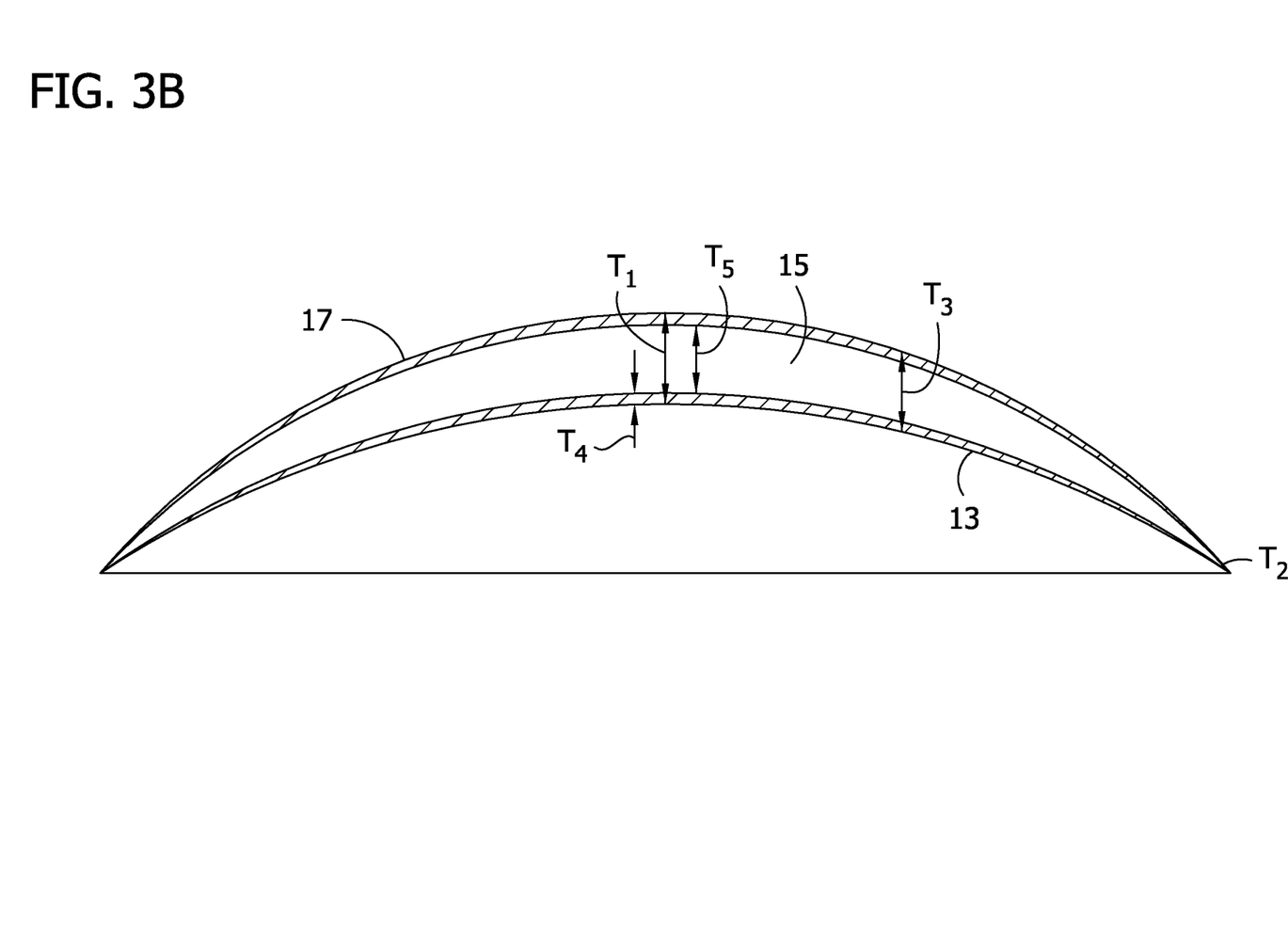
FIG. 3B is and cross-sectional view of the breast pad.

In one embodiment, and with reference to FIG. 3B, the pad 11 has a maximum thickness $T_1$ of between about 0.2 inches (0.5 cm) and about 0.4 inches (1 cm). In one embodiment, the pad 11 has a maximum thickness $T_1$ of at least about 0.25 inches (0.6 cm). In one embodiment, the pad 11 has a maximum thickness $T_1$ of about 0.25 inches (0.6 cm). The maximum thickness may be located generally at a center of the pad. The thickness of the pad 11 tapers from the center of the pad to the edge of the pad. In one embodiment, the pad has a minimum thickness $T_2$ at the edge of the pad of between about 0.05 inches (0.1 cm) and about 0.08 inches (0.2 cm). In one embodiment, the pad 11 has a minimum thickness $T_2$ of no more than about 0.08 inches (0.2 cm). In one embodiment, the pad 11 has a minimum thickness $T_2$ of about 0.06 inches (0.15 cm). An intermediate location about midway between the center of the pad 11 and the edge of the pad may have a thickness $T_3$ of between about 0.1 inches (0.2 cm) and about 0.2 inches (0.5 cm). In one embodiment, the thickness $T_3$ is about 0.125 inches (0.3 cm).

Referring to FIGS. 3-3B, the inner layer 13 can be constructed of a material that is capable of wicking moisture away from a subject's breast. The inner (or "wicking") layer 13, through capillary action, draws in the secreted breast milk, and carries the milk away from the breast, transporting the moisture from locations on the breast near the inner layer, where the breast milk is most abundant (e.g., nipple), across the wicking layer 13 away from the more saturated areas to the dry/less saturated areas of the wicking layer. In the illustrated embodiment, the wicking layer 13 comprises a one-way wicking material. An inner surface 21, disposed for contacting the subject's breast, includes hydrophilic fibers 23 that first contact the breast milk to wick the milk across the wicking layer and through the wicking layer away from the breast. An outer surface 25 of the wicking layer 13 includes hydrophobic fibers 27 that hold the breast milk at the outer surface keeping the breast milk from traveling back through the wicking layer to the subject's breast. Suitable wicking materials may include, for example, some forms of polyester, polypropylene, and/or other materials. Microfibers may also be used. Suitable wicking materials include, but are not limited to, ProCool® Stretch-FIT Sports Jersey Fabric and ProCool® Dri-QWick™ Sports Mesh Fabric, sold by AKAS Tex of Bensalem, PA In one embodiment, the inner wicking layer 13 has a maximum thickness $T_4$ (FIG. 3B) of between about 0.05 inches (0.13 cm) and about 0.07 inches (0.18 cm).

The intermediate layer 15 can be formed from an absorbent material such as materials including cellulosic fibers (e.g., cotton, hemp, Tencel™, bamboo, etc.) The cellulosic fibers may be interspersed within a polyester and/or nylon matrix. Alternatively, the absorbent material may be a semi-closed or closed cell hydrophilic polyurethane foam or the like. In one embodiment, the intermediate layer 15 may comprise Capu-Cell® polyurethane foam sold by Foam Sciences of Buffalo, NY. The semi-closed cell, hydrophilic polyurethane foam is capable of absorbing up to 15 times its weight in fluid. Further, the foam material is capable of superior absorbance while having a relatively small thickness in comparison to conventional cotton absorbent layers. In one embodiment, the foam absorbent layer 15 has a maximum thickness $T_5$ of between about 0.18 inches (0.46 cm) and about 0.37 inches (0.94 cm). In addition, foam is cheaper and allows for a wider variety of shapes for the intermediate layer 15 than is afforded by a cotton-based layer. Additionally, the foam releases liquid only under pressure in part due to its matrix construction including small cells having thousands of sizes. Continued pressure draws fluid into the smaller cells after the larger cells are filled. Thus, the absorbent layer 15 is configured to hold fluid, such as breast milk, away from the subject's skin. Therefore, the breast milk that is wicked from the subject's breast from the inner surface 21 to the outer surface 25 of the wicking layer 13 is then absorbed by the intermediate layer 15. As used in the present disclosure, "absorbent" refers to a characteristic of a material whereby the material takes in moisture with little to no transfer of the moisture within the material. Accordingly, the absorbent material of the intermediate layer 15 will eventually become saturated if kept in constant contact with fluid, as compared to a wicking material that transports fluid within the material.

The outer cover 17 of the pad 11 overlies the intermediate layer 15 and functions to hold any moisture in the pad. As such, the outer cover 17 is liquid impermeable so that the fluid (e.g., breast milk) absorbed by the intermediate layer 15 does not escape the pad 11 through the outer cover. A suitable material for the outer cover 17 may be polyurethane. In one embodiment, the outer cover 17 is a polyurethane laminate. Other liquid impermeable materials for the outer cover 17 are also envisioned without departing from the scope of the disclosure.

As used herein, the terms "proximal", "distal", and "intermediate" represent relative locations of components, parts and the like of the breast pad when the pad is placed over the subject's breast. As such, a "proximal" component or the like is disposed most adjacent to a point of contact with the subject's breast, a "distal" component is disposed most distant from the point of contact, and an "intermediate" component is disposed generally anywhere between the proximal and distal components.

Figure 4:
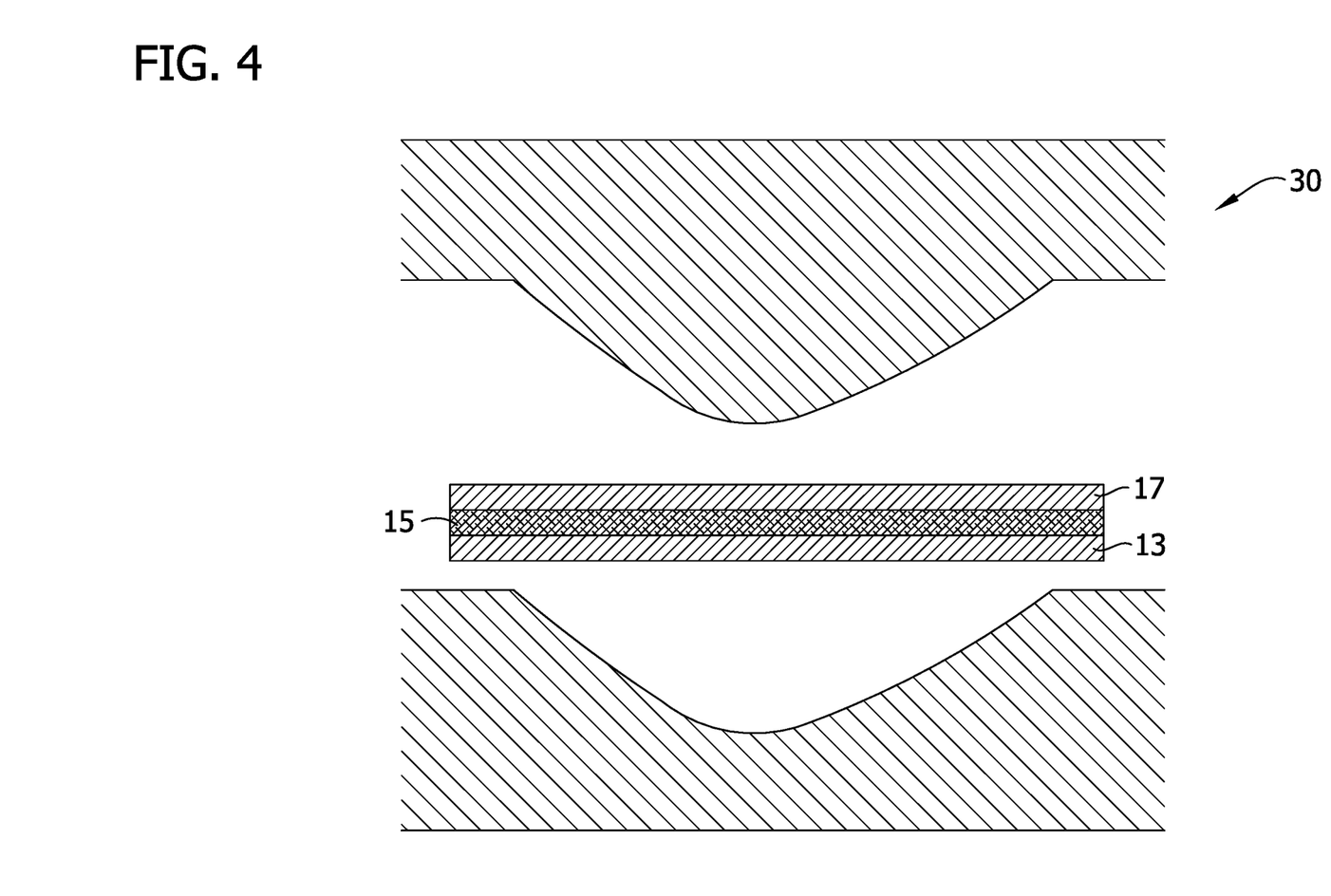
FIG. 4 is a schematic representation of layers of the breast pad being bonded together by thermoforming.

Referring to FIG. 4, the layers 13, 15, 17 of the pad 11 can be bonded together using a thermoforming process. In this process, intermediate layer 15 may be overlaid on the inner layer 13, and the outer cover 17 may be overlaid on the intermediate layer. The inner layer 13 and outer cover 17 may be bonded to the intermediate layer 15 prior to the thermoforming process. For example, a hot melt solvent-free adhesive coating may be applied between the layers to bond the layers together. The layers 13, 15, 17 are then placed within a mold 30 having the desired shape of the pad 11. The pad 11 may have a generally concave teardrop shape to follow the natural curve of a subject's breast. Thus, the mold would be suitably constructed to produce the desired shape. Still other shapes for the pad 11 are envisioned such as round or circular, oblong, and rectangular without departing from the scope of the disclosure. In one embodiment, the pad may be circular with a diameter of at least about 4.6 inches (12 cm).

After the layers 13, 15, 17 are placed in the mold 30, the mold is pressed over the layers to set the layers into the shape of the mold. The layers 13, 15, 17 are then heated within the mold 30 to a sufficient temperature so that the layers become pliable for conforming to the shape of the mold. Thus, the layers 13, 15, 17 are heat set within the mold. In one embodiment, the layers 13, 15, 17 are heated to a temperature less than about 350 degrees F. In one embodiment, the layers 13, 15, 17 are heated to a temperature between about 320 degrees F. and about 340 degrees F. In one embodiment, the layers 13, 15, 17 are heated to a temperature of about 340 degrees F. The layers 13, 15, 17 are also held within the mold for a predetermined amount of time. For example, the layers 13, 15, 17 may be held in the mold for a dwell time of about 1 to 3 minutes. In one embodiment, the dwell time is between about 1.5 and about 2 minutes.

When the layers 13, 15, 17 are removed from the mold, they retain the shape in which they were formed. The pad 11 may be further trimmed as necessary to produce the final shape of the pad. To this effect, the layers 13, 15, 17 of the pad 11 may be bonded together without the use of any stitching that produces seam lines that can harbor bacteria. However, stitching can be used without departing from the scope of the disclosure. Accordingly, the thermoforming process produces a safer and more sanitary pad 11 than would be formed by conventional forming methods. Also, by thermoforming the layers 13, 15, 17 together the pad 11 is able to maintain the structural integrity of each individual layer contributing to the overall durability of the pad. As such, the pad 11 is able to withstand repeated use making the pad suitable as a reusable pad. Further, because the structural integrity of each individual layer is maintained, the pad 11 can be washed between uses without compromising the integrity of the pad or altering the shape.

Additionally or alternatively, a breathable polyurethane material (not shown) may be disposed between the inner layer 13 and the intermediate layer 15. The breathable polyurethane material may be formed in any suitable manner such as by forming perforations through a layer of polyurethane material. Still other means of forming the breathable polyurethane material are without the scope of the disclosure. In this embodiment, the thermoforming process can be performed without the use of any adhesive between the layers. Thus, the polyurethane material is overlaid on the inner layer, the intermediate layer 15 may be overlaid on the polyurethane material, and the outer cover 17 may be overlaid on the intermediate layer. This arrangement is then placed in the mold 30 without previously bonding the layers together using an adhesive.

Additionally, some or all of the layers 13, 15, 17 could be treated with an antimicrobial coating to prevent the growth of bacteria. The prevention of bacteria growth may also help control the odor of the pad 11. In one embodiment, the inner layer 13 and outer layer 17 may be treated with an antimicrobial coating. In one embodiment, the coating may be formed from SILVADUR™.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A breast pad for receiving fluid leaked from a subject's breast, the breast pad comprising:
   an inner layer disposed for contacting the subject's breast, the inner layer having an inner surface and an outer surface opposite the inner surface, the inner layer comprising wicking material for wicking fluid from the inner surface to the outer surface away from the subject's breast,
   an intermediate layer disposed over the outer surface of the inner layer, the intermediate layer comprising an absorbent material including a semi-closed cell hydrophilic polyurethane foam for absorbing the fluid wicked from the subject's breast by the wicking material of the inner layer; and
   an outer layer disposed over the intermediate layer, the outer layer comprising a liquid-impermeable material for trapping the fluid absorbed by the intermediate layer within the breast pad, the inner layer, intermediate layer, and outer layer being bonded together;
   wherein the breast pad is washable without compromising an integrity of the breast pad or altering a shape of the breast pad such that the breast pad can be reused.

2. The breast pad of claim 1 wherein the inner surface of the inner layer includes hydrophilic fibers, and the outer surface of the inner layer includes hydrophobic fibers.

3. The breast pad of claim 1 wherein the intermediate layer is disposed directly over the inner layer, and the outer layer is disposed directly over the intermediate layer.

4. The breast pad of claim 1 wherein the outer layer comprises a polyurethane laminate.

5. The breast pad of claim 1 wherein the inner layer, intermediate layer, and outer layer are thermoformed.

6. The breast pad of claim 5 wherein the breast pad is seamless such that the breast pad is free of any seam lines.

7. The breast pad of claim 1 wherein each layer comprising a polymer material.

8. The breast pad of claim 1 further comprising a solvent-free adhesive between the layers to bond the layers together.

9. The breast pad of claim 1 wherein layers of the pad consist only of the inner layer, intermediate layer, and outer layer.

10. The breast pad of claim 1 wherein the pad has a maximum thickness of between about 0.2 inches (0.5 cm) and about 0.4 inches (1 cm).

11. The breast pad of claim 1 wherein the layers are treated with an antimicrobial coating.

12. A breast pad for receiving fluid leaked from a subject's breast, the breast pad comprising a wicking layer, an absorbent layer comprising a semi-closed cell hydrophilic polyurethane foam disposed over the wicking layer, and a liquid-impermeable layer disposed over the absorbent layer, the layers being thermoformed to bond the layers together, the wicking layer, absorbent layer, and liquid-impermeable layer being bonded together, wherein the breast pad is washable without compromising an integrity of the breast pad or altering a shape of the breast pad such that the breast pad can be reused.

13. The breast pad of claim 12 wherein the breast pad is seamless such that the breast pad is free of any seam lines.

14. The breast pad of claim 12 wherein the layers are treated with an antimicrobial coating.

15. The breast pad of claim 12 further comprising a solvent-free adhesive between the layers to bond the layers together.

16. The breast pad of claim 12 wherein each layer comprising a polymer material.

17. A method of making a breast pad comprising:
   providing a wicking layer;
   overlaying an absorbent layer comprising a semi-closed cell hydrophilic polyurethane foam on the wicking layer;
   overlaying a liquid-impermeable outer layer on the absorbent layer;
   pressing the wicking layer, absorbent layer, and outer layer together in a mold; and
   heating the wicking layer, absorbent layer, and outer layer in the mold to deform and set the layers into a desired shape; and
   bonding the absorbent layer to the wicking layer before pressing the layers together in the mold;
   wherein the breast pad is washable without compromising an integrity of the breast pad or altering a shape of the breast pad such that the breast pad can be reused.

18. The method of claim 17, further comprising heating the wicking layer, absorbent layer, and outer layer to between about 320 and about 340 degrees F. in the mold.

* * * * *